United States Patent [19]

De Bellis

[11] 4,388,930
[45] Jun. 21, 1983

[54] CARDIAC CATHETER ELECTRODES FOR PACEMAKERS PROVIDED WITH A CARDIAC RF RECEIVER FOR EMERGENCY PACING

[75] Inventor: Ferruccio De Bellis, Rome, Italy

[73] Assignee: S.B.M. Societa Brevetti per la Medicina S.R.L., Italy

[21] Appl. No.: 303,596

[22] Filed: Sep. 18, 1981

[30] Foreign Application Priority Data

Oct. 7, 1980 [IT] Italy ............................... 49838 A/80

[51] Int. Cl.³ ............................................. A61N 1/36
[52] U.S. Cl. ............................................. 128/419 PS
[58] Field of Search ................... 128/419 PG, 419 PS, 128/419 P

[56] References Cited

U.S. PATENT DOCUMENTS

| | | | |
|---|---|---|---|
| 3,311,111 | 3/1967 | Bowers | 128/419 PG |
| 3,357,434 | 12/1967 | Abell | 128/419 PG |
| 3,717,152 | 2/1973 | Van Den Berg | 128/419 PG |
| 4,341,226 | 7/1982 | Peters | 128/419 P |

Primary Examiner—William E. Kamm
Attorney, Agent, or Firm—Bacon & Thomas

[57] ABSTRACT

A catheter electrode for pacemakers provided with an integrally formed cardiac receiver for emergency pacing at radio frequency (RF), which catheter electrode has the pacemaker at one end and the pacing tip at the other end, wherein the RF cardiac receiver is connected thereto at an intermediate position between its two ends by clamping its coil onto the coiled wire of the electrode which has been previously exposed through removal of a short length of the insulating sheath so called spaghetti.

5 Claims, 2 Drawing Figures

CARDIAC CATHETER ELECTRODES FOR PACEMAKERS PROVIDED WITH A CARDIAC RF RECEIVER FOR EMERGENCY PACING

This invention relates to an improved catheter electrode for pacemakers provided with an RF cardiac receiver connected thereto without breaking off the mechanical continuity of the electrode.

Known catheter electrodes now used in connection with pacemakers provided with parallel cardiac receivers are Y-shaped and therein the pacing tip is located at the end of the Y "stem", the pacemaker is located at the end of one arm, while the receiver is located at the end of the other arm. Usually, in these catheters one of the arms of the Y and the stem thereof carrying the pacing tip are made from an integral long length of catheter electrode and form the main branch thereof, while the other arm of the Y consists in a shorter length of the catheter electrode and it is connected to the main branch at an intermediate position.

These Y-shaped catheter electrodes according to the prior art and structured as mentioned above have a drawback in that the connection of the cardiac receiver to one of the Y arms must be carried out during installation of the pacemaker in the patient, thus unduly lengthening the procedure time. Furthermore, the junction of the other Y arm to the main branch of the catheter electrode forms a critical point which is inherently weak.

The improved catheter electrode of the invention is free from the above-mentioned drawback since the RF cardiac receiver is connected on manufacturing the catheter electrode instead of being connected during the installation thereof and furthermore the same has the advantage that the cardiac receiver coil is extremely reduced in size. This small-sized cardiac receiver coil needs an accordingly reduced receiving "pocket" to be formed in the patient's subcutaneous connective tissue, with evident benefits to the patient himself.

Accordingly, the improved catheter electrode of the invention comprises an integrally formed catheter electrode carrying the pacemaker at one end and the pacing tip at the other end and it has a parallel inserted small-sized cardiac receiver.

The cardiac receiver comprises the coil unit connected to the catheter electrode at a suitable intermediate position between the two ends thereof and an outer case applied thereon after the coil has been connected to the catheter electrode. Connection of the coil to the catheter electrode is carried out by clamping the coil onto the catheter electrode wire previously exposed by removing a short length of the spaghetti.

Accordingly, the catheter electrode crosses the cardiac receiver protective outer case which thus completely encloses both the coil unit and a small length of the catheter electrode adjacent to the spaghetti area removed to expose the inner wire.

The RF cardiac receiver located on the catheter electrode is preferably placed about 55 cm from the pacing tip. The other length of the catheter electrode, the end of which is to be connected to the pacemaker, is preferably about 60 cm long and it can be cut to the suitable size according to the characteristics of istallation of the pacemaker.

According to the invention the RF cardiac receiver is inserted in the patient's breast area about where the catheter electrode enters the vein, while the operator is free to decide where to implant the pacemaker connected to the other end of the catheter electrode.

The invention will be now described in detail with reference to the annexed drawing, wherein.

Figure 1:
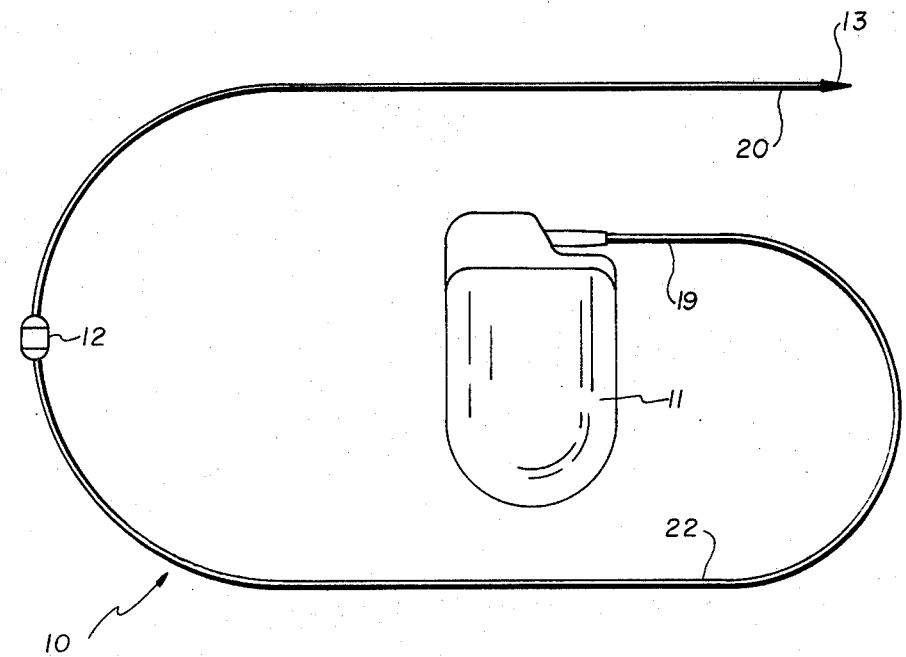
FIG. 1 is an overall view of the catheter electrode of the invention.

Referring to FIG. 1, the catheter provided with an RF cardiac receiver for emergency pacing according to the invention comprises an integral length of the catheter electrode referred to by 10, a pacemaker 11, an RF cardiac receiver 12 and a pacing tip 13.

Length 10 of the catheter electrode usually comprises a spaghetti 14 (FIG. 2) receiving the conductive portion 15 comprising a thin wire which is short-pitch coiled in order to provide the required flexibility.

Pacemaker 11 is conventional and it will not be further described herein. Cardiac receiver 12 comprises a case 16 and a coil unit including a coil schematically referred to by 18 and various components associated thereto for its operation.

Pacemaker 11 is connected to the proximal end 19 of the catheter electrode length and pacing tip 13 is connected to distal end 20 thereof.

Figure 2:
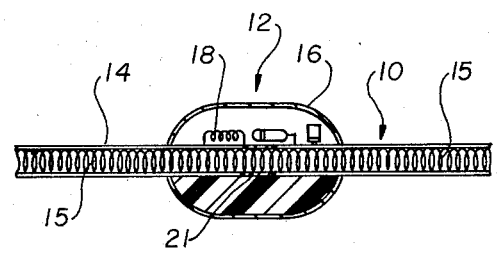
FIG. 2 is a sectional view of a detail showing the structure of the RF cardiac receiver used in connection with the catheter electrode of the invention and the corresponding length of the latter to which the receiver is connected.

As it can be readily seen in the drawing and particularly in FIG. 2, cardiac receiver 12 is connected at an intermediate position to catheter electrode 10 without breaking off either the mechanical or the electrical continuity of the electrode.

This connection is carried out by removing a short length of spaghetti 14 so as to expose inner wire 15 and then electrically connecting coil 18 onto wire 15 through a clamping operation, as schematically indicated at 21.

Case 16 of cardiac receiver made of a suitable thermoplastic resin such as araldite is then applied on the junction of the coil unit to wire 15 and the adjacent length of the catheter electrode.

As mentioned above, cardiac receiver 12 will be located about 55 cm from pacing tip 13, while length 22 of catheter electrode 10 which is about 60 cm long will be cut to size according to the characteristics of installation of the pacemaker and before the connection of the latter to the catheter electrode.

I claim:

1. A catheter electrode for pacemakers provided with a parallel RF cardiac receiver for emergency pacing at radio frequency comprising an integral length of catheter electrode including an inner conductive portion comprising a coiled wire and an outer sheath so called spaghetti, the pacemaker being located at one end and the pacing tip being located at the other end of said catheter electrode, wherein the small-sized coil unit of said RF cardiac receiver is directly connected to said length of the catheter electrode at a suitable position between said two ends thereof and a small portion of said inner wire is exposed through removal of a corresponding area of said spaghetti.

2. The catheter electrode according to claim 1, wherein said cardiac receiver coil is connected to said previously exposed wire of the catheter electrode through a clamping operation.

3. The catheter electrode according to claim 2, wherein the outer case of said RF cardiac receiver which is made of a suitable thermoplastic resin is so applied on said coil unit connected to said catheter electrode wire as to enclose both said coil unit and a small length of the catheter electrode adjacent to the junction thereof.

4. The catheter electrode according to claim 1, wherein said cardiac receiver is connected to said catheter electrode preferably about 50-60 cm from the catheter electrode end carrying the pacing tip.

5. The catheter electrode according to claim 4, wherein said connection is made 55 cm from said end carrying said pacing tip.

* * * * *